(12) United States Patent
Sniadecki et al.

(10) Patent No.: US 9,213,024 B2
(45) Date of Patent: Dec. 15, 2015

(54) MICROFLUIDIC DEVICES FOR MEASURING PLATELET COAGULATION AND ASSOCIATED SYSTEMS AND METHODS

(71) Applicant: University of Washington through its Center for Commercialization, Seattle, WA (US)

(72) Inventors: Nathan J. Sniadecki, Bothell, WA (US); Lucas H. Ting, Seattle, WA (US); Shirin Feghhi, Seattle, WA (US); Kevin S. Bielawski, Seattle, WA (US); Nathan J. White, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/126,412

(22) PCT Filed: Mar. 14, 2013

(86) PCT No.: PCT/US2013/031782
§ 371 (c)(1),
(2) Date: Dec. 13, 2013

(87) PCT Pub. No.: WO2013/169379
PCT Pub. Date: Nov. 14, 2013

(65) Prior Publication Data
US 2015/0056643 A1    Feb. 26, 2015

Related U.S. Application Data

(63) Continuation of application No. 13/663,339, filed on Oct. 29, 2012.

(60) Provisional application No. 61/760,849, filed on Feb. 5, 2013, provisional application No. 61/709,809, filed on Oct. 4, 2012, provisional application No. 61/645,191, filed on May 10, 2012.

(51) Int. Cl.
*C12M 1/00*     (2006.01)
*G01N 15/06*    (2006.01)
(Continued)

(52) U.S. Cl.
CPC .......... *G01N 33/4905* (2013.01); *C12M 35/04* (2013.01); *C12M 41/46* (2013.01);
(Continued)

(58) Field of Classification Search
CPC .......... G01N 33/4905; G01N 33/5302; C12M 35/04; C12M 41/46
USPC ....................... 435/4, 283.1, 288.5
See application file for complete search history.

(56) References Cited

U.S. PATENT DOCUMENTS

| 4,986,964 A | 1/1991 | Carr, Jr. et al. |
| 5,205,159 A | 4/1993 | Carr, Jr. |

(Continued)

FOREIGN PATENT DOCUMENTS

| EP | 2208531    | 7/2010 |
| EP | 2208531 A1 | 7/2010 |

(Continued)

OTHER PUBLICATIONS

International Search Report and Written Opinion mailed Oct. 22, 2014 in International Patent Application No. PCT/US2014/044448, 15 pages.

(Continued)

*Primary Examiner* — Betty Forman
(74) *Attorney, Agent, or Firm* — Perkins Coie LLP (57) ABSTRACT

The present technology relates generally to microfluidic devices for measuring platelet coagulation, and associated systems and methods. In some embodiments, a fluidics device includes an array of microstructures including pairs of generally rigid blocks and generally flexible posts. The fluidics device further includes at least one fluid channel configured to accept the array. The fluid channel is configured to induce fluid flow of a biological sample, such as whole blood, through the array. The fluidics device can further include a detection component configured to measure a degree of deflection of one or more of the flexible posts in the array. In some embodiments, the fluidics device comprises a handheld device and usable for point of care testing of platelet forces and coagulation.

21 Claims, 6 Drawing Sheets

(51) Int. Cl.

| | |
|---|---|
| *C12Q 1/68* | (2006.01) |
| *G01N 33/49* | (2006.01) |
| *G01N 33/53* | (2006.01) |
| *C12M 1/42* | (2006.01) |
| *C12M 1/34* | (2006.01) |
| *G01N 15/14* | (2006.01) |
| *B01L 3/00* | (2006.01) |
| *G01N 15/10* | (2006.01) |

(52) U.S. Cl.
CPC ........ *G01N15/1056* (2013.01); *G01N 15/1459* (2013.01); *G01N 15/1463* (2013.01); *G01N 33/5302* (2013.01); *B01L 3/502746* (2013.01); *G01N 15/1404* (2013.01); *G01N 2015/1006* (2013.01)

(56) References Cited

U.S. PATENT DOCUMENTS

| | | | |
|---|---|---|---|
| 6,573,104 | B2 | 6/2003 | Carr, Jr. et al. |
| 7,163,659 | B2 | 1/2007 | Stasiak et al. |
| 7,192,726 | B1 | 3/2007 | Carr, Jr. et al. |
| 7,670,831 | B2 | 3/2010 | Lee et al. |
| 7,774,951 | B2 | 8/2010 | Hartmann et al. |
| 8,187,865 | B2 | 5/2012 | Yun et al. |
| 8,278,919 | B2 * | 10/2012 | Fischer et al. ............. 324/244 |
| 2002/0172963 | A1 | 11/2002 | Kelley et al. |
| 2002/0187504 | A1 | 12/2002 | Reich et al. |
| 2003/0044853 | A1 | 3/2003 | Socks et al. |
| 2003/0092016 | A1 * | 5/2003 | Wiggins et al. ................ 435/6 |
| 2003/0097120 | A1 | 5/2003 | Santerre |
| 2003/0154771 | A1 | 8/2003 | de Charmoy Grey et al. |
| 2003/0215816 | A1 | 11/2003 | Sundararajan et al. |
| 2004/0151629 | A1 * | 8/2004 | Pease et al. ................ 422/68.1 |
| 2005/0015001 | A1 | 1/2005 | Lec et al. |
| 2005/0019791 | A1 | 1/2005 | Jung et al. |
| 2006/0063153 | A1 | 3/2006 | Mamine et al. |
| 2006/0121502 | A1 * | 6/2006 | Cain et al. ..................... 435/6 |
| 2007/0194658 | A1 | 8/2007 | Zhang et al. |
| 2007/0235340 | A1 | 10/2007 | Naughton |
| 2008/0026476 | A1 | 1/2008 | Howell et al. |
| 2008/0160548 | A1 | 7/2008 | Klapproth |
| 2008/0234236 | A1 | 9/2008 | Veltri et al. |
| 2008/0261261 | A1 | 10/2008 | Grimes et al. |
| 2009/0045063 | A1 * | 2/2009 | Kang et al. .................... 204/556 |
| 2009/0130744 | A1 | 5/2009 | Saldivar et al. |
| 2009/0181421 | A1 | 7/2009 | Kapur et al. |
| 2010/0006439 | A1 | 1/2010 | Ham et al. |
| 2010/0324838 | A1 | 12/2010 | Hartmann et al. |
| 2011/0189719 | A1 | 8/2011 | Kuo et al. |
| 2011/0203367 | A1 | 8/2011 | Huang et al. |
| 2012/0015368 | A1 | 1/2012 | Del Galdo et al. |
| 2012/0058500 | A1 | 3/2012 | Mitchell et al. |
| 2012/0071342 | A1 | 3/2012 | Lochhead et al. |
| 2012/0142556 | A1 | 6/2012 | Parker et al. |
| 2012/0156791 | A1 * | 6/2012 | Superfine et al. .............. 436/69 |
| 2012/0161207 | A1 | 6/2012 | Homyk et al. |
| 2012/0212732 | A1 | 8/2012 | Santori et al. |
| 2013/0109012 | A1 | 5/2013 | Sniadecki et al. |
| 2013/0237453 | A1 | 9/2013 | Chander |

FOREIGN PATENT DOCUMENTS

| | | |
|---|---|---|
| WO | 02090976 | 11/2002 |
| WO | 2004062570 | 7/2004 |
| WO | 2004093641 | 11/2004 |
| WO | 2006055318 | 5/2006 |
| WO | 2006055318 A2 | 5/2006 |
| WO | 2006084242 | 8/2006 |
| WO | 2008103430 | 8/2008 |
| WO | 2010151780 | 12/2010 |
| WO | 2012048288 | 4/2012 |
| WO | 2012048288 A1 | 4/2012 |
| WO | 2013076157 | 5/2013 |
| WO | 2013076157 A1 | 5/2013 |

OTHER PUBLICATIONS

Kantak et al., "Microfuidic platelet function analyzer for shear-induced platelet activation studies," 2nd Annual Intl IEEE-EMBS Spcl Topic Conf on Microtech in Med and Bio, Jan. 1, 2002, pp. 169-173.
Gutierrez et al., "Microfulidic devices for studies of shear-dependent platelet adhesion," Lab on a Chip, (8) 9: 1486 (2008).
Conant et al., "Well plate microfulidic system for investigation of dynamic platelet behavior under variable shear loads," Biotech and Bioengineering, (108) 12: 2978-2987 (2011).
Feghhi et al., "Mechanobiology of Platelets: Techniques to Study the Role of Fluid Flow and Platelet Retraction Forces at the Micro- and Nano-Scale," Intl Jnl of Molecular Sciences, (12) 12: 9009-9030 (2011).
Alevriadou et al. (1993) Real-time analysis of shear-dependent thrombus formation and its blockade by inhibitors of von Willebrand factor binding to platelets. Blood 81(5):1263-1276.
Alon et al. (2007) Force as a facilitator of integrin conformational changes during leukocyte arrest on blood vessels and antigen-presenting cells. Immunity. 26(1): p. 17-27.
Anand et al. (2006) A viscoelastic fluid model for describing the mechanics of a coarse ligated plasma clot Theoretical and Computational Fluid Dynamics. 20(4): p. 239-250.
Arias-Salgado et al. (2008) Variations in platelet protein associated with arterial thrombosis. Thromb Res. 122(5): p. 640-647.
Back et al. (1977) Analysis of pulsatile, viscous blood flow through diseased coronary arteries of man. J Biomech 10(5-6):339-353.
Barg et al. (2007) Soluble plasma-derived von Willebrand factor assembles to a haemostatically active filamentous network. Thromb Haemost 97(4):514-526.
Baselt et al. (1998). A biosensor based on magnetoresistance technology. Biosensors & Bioelectronics 13(7-8): 731-739.
Basmadjian, D. (1984) The hemodynamic forces acting on thrombi, from incipient attachment of single cells to maturity and embolization. J Biomech. 17(4): p. 287-298.
Basmadjian, D. (1986) The hemodynamic and embolizing forces acting on thrombi—II. The effect of pulsatile blood flow. J Biomech. 19(10): p. 837-845.
Basmadjian, D. (1989) Embolization: critical thrombus height, shear rates, and pulsatility. Patency of blood vessels. Journal of Biomedical Materials Research. 23(11 ): p. 1315-1326.
Brass et al. (2005) Minding the gaps to promote thrombus growth and stability. J Clin Invest. 115(12): p. 3385-3392.
Brohi et al. (2008). Acute coagulopathy of trauma: hypoperfusion induces systemic anticoagulation and hyperfibrinolysis. J Trauma 64(5): 1211-1217; discussion 1217.
Brohi et al. Acute traumatic coagulopathy. J Trauma 54, 1127-1130, (2003).
Calaminus et al. (2007) Myosinlla contractility is required for maintenance of platelet structure during spreading on collagen and contributes to thrombus stability. J Thromb Haemost. 5(10): p. 2136-2145.
Carr et al. (1991) Measurement of platelet-mediated force development during plasma clot formation. Am J Med Sci. 302(1): p. 13-18.
Carr et al. (2002) Enhanced platelet force development despite drug-induced inhibition of platelet aggregation in patients with thromboangiitis obliterans—two case reports. Vasc Endovascular Surg. 36(6): p. 473-480.
Carr, M.E. (2004) Monitoring Hemostasis in Combat Trauma Patients. Military Medicine. 169(12): p. 11-15.
Carr, M.E., Jr. (2003) Development of platelet contractile force as a research and clinical measure of platelet function. Cell Biochem Biophys. 38(1 ): p. 55-78.
Carroll et al. (2009) Early evaluation of acute traumatic coagulopathy by thrombelastography. Transl Res. 154(1): p. 34-39.
Chien S. Effects of disturbed flow on endothelial cells. Ann Biomed Eng 36: 554-562, 2008.
Chiu et al. Effects of disturbed flow on endothelial cells. J Biomech Eng 120: 2-8, 1998.

(56) References Cited

OTHER PUBLICATIONS

Chu et al. Force measurements in E-cadherin-mediated cell doublets reveal rapid adhesion strengthened by actin cytoskeleton remodeling through Rac and Cdc42. J Cell Biol 167: 1183-1194, 2004.
Cohen et al. (1973) Platelet contractile regulation in an isometric system. Nature. 246(5427): p. 36-37.
Cohen et al. (1982) Ultrastructure of clots during isometric contraction. J Cell Biol. 93(3): p. 775-787.
Cohen et al. (1989) The effect of peptides and monoclonal antibodies that bind to platelet glycoprotein llb-llla complex on the development of clot tension. Blood. 73(7): p. 1880-1887.
Counts et al. (1979) Hemostasis in massively transfused trauma patients. Ann Surg. 190(1): p. 91-99.
Dai et al. Distinct endothelial phenotypes evoked by arterial waveforms derived from atherosclerosis-susceptible and -resistant regions of human vasculature. Proc Natl Acad Sci US A 101: 14871-14876, 2004.
Dasta et al. (2005). Daily cost of an intensive care unit day: the contribution of mechanical ventilation. Critical Care Medicine 33(6): 1266-1271.
Davies PF. Flow-mediated endothelial mechanotransduction. Physiological Reviews 75: 519-560, 1995.
Dayananda et al. (2010) von Willebrand factor self-association on platelet Gplbalpha under hydrodynamic shear: effect on shear-induced platelet activation. Blood 116(19):3990-3998.
Dejana E. Endothelial cell-cell junctions: happy together. Nat Rev Mol Cell Biol 5: 261-270, 2004.
Desai et al. (2007) Microfabricated Post-Array-Detectors (mPADs): An Approach to Isolate Mechanical Force. Journal of Visualized Experiments. (7) p. 1-4.
Doggett et al. (2002) Selectin-like kinetics and biomechanics promote rapid platelet adhesion in flow: the GPib(alpha)-vWF tether bond. Biophys J 83(1):194-205.
Dopheide, et al. Shear-dependent tether formation during platelet translocation on von Willebrand factor. Blood, 2002. 99(1): p. 159-167.
Dudek et al. Cytoskeletal regulation of pulmonary vascular permeability. J Appl Physiol 91: 1487-1500, 2001.
Duffy et al. (1998) Rapid prototyping of microfluidic systems in poly(dimethylsiloxane). Analytical Chemistry. 70(23): p. 4974-4984.
Fabian et al. an enhancer of myosin, speeds up anaphase chromosome movement. Cell Chromosome 6: 1, 2007.
Feghhi et al. (2011). Mechanobiology of Platelets: Techniques to Study the Role of Fluid Flow and Platelet Retraction Forces at the Micro- and Nano-Scale. International Journal of Molecular Sciences 12(12): 9009-9030.
Feng et al. (2006) Pathological shear stress directly regulates platelet alphaIlbbeta3 signaling. Am J Physiol Cell Physiol 291(6):C1346-1354.
Freitas et al. (2007). Magnetoresistive sensors. Journal of Physics-Condensed Matter 19(16).
Frith et al. (2012). Acute traumatic coagulopathy. Current Opinion in Anesthesiology 25(2): 229-234.
Furie, et al. (2008) Mechanisms of thrombus formation. N Engl J Med. 359(9): p. 938-949.
Ganter et al. (2008). Coagulation monitoring: current techniques and clinical use of viscoelastic point-of-care coagulation devices. Anesth Analg 106(5): 1366-1375.
Geiger et al. (2001) Transmembrane extracellular matrix-cytoskeleton crosstalk. Nat Rev Mol Cell Biol. 2(11): p. 793-805.
Gimbrone MA. The Gordon Wilson lecture: Understanding vascular endothelium: a pilgrim's progress: endothelial dysfunction, biomechanical forces and the pathobiology of atherosclerosis. Trans Am Clin Climatol Assoc 121: 115-127; discussion 127, 2010.
Gomez-Sjoberg et al. (2007) Versatile, fully automated, microfluidic cell culture system. Anal Chem. 79(22): p. 8557-8563.
Greilich et al. (1995) Reductions in platelet force development by cardiopulmonary bypass are associated with hemorrhage. Anesth Analg. 80(3): p. 459-465.
Griffiths et al. (2001) Low dispersion turns and junctions for microchannel systems. Analytical Chemistry. 73(2): p. 272-278.
Grunkemeier et al. (2000) The effect of adsorbed fibrinogen, fibronectin, von Willebrand factor and vitronectin on the procoagulant state of adherent platelets. Biomaterials. 21(22): p. 2243-2252.
Haenecke et al. (2007) Thrombelastography today: Practicability and analytical power. Transfusion Medicine and Hemotherapy. 34(6): p. 421-428.
Hahn et al. Mechanotransduction in vascular physiology and atherogenesis. Nat Rev Mol Cell Biol 10: 53-62, 2009.
Harris et al. (2000) The leukocyte integrins. J Biol Chem. 275(31): p. 23409-23412.
Hartman et al. (2009) Cluster size regulates protein sorting in the immunological synapse. Proc Natl Acad Sci U S A. 106(31): p. 12729-12734.
Holcomb et al. (2012). Admission rapid thrombelastography can replace conventional coagulation tests in the emergency department: experience with 1974 consecutive trauma patients. Ann Surg. 256(3): 476-486.
http://www.who.int/entity/healthinfo/global_burden_disease/gbd-deathdalycountryestimates.2004.xls, World Health Org., Department Measurement and Health Information; Feb. 2009.
Inoue et al (2008) Redundant mechanism of platelet adhesion to laminin and collagen under flow: involvement of von Willebrand factor and glycoprotein Ib-IX-V. J Biol Chem. 283(24): p. 16279-16282.
Inoue et al. (2006) Laminin stimulates spreading of platelets through integrin alpha6beta1-dependent activation of GPVI. Blood. 107(4): p. 1405-1412.
Jackson et al. (2009) Dynamics of platelet thrombus formation. J Thromb Haemost. 7 Suppl 1: p. 17-20.
Jackson, SP (2011) Arterial thrombosis—insidious, unpredictable and deadly. Nat Med 17(11):1423-1436.
Jacoby et al. Platelet activation and function after trauma. J Trauma 51, 639-647, (2001).
Jiang et al. Ultralow-fouling, functionalizable, and hydrolyzable zwitterionic materials and their derivatives for biological applications. Adv Mater 22, 920-932, (2010).
Kashuk et al. (2010) Postinjury coagulopathy management: goal directed resuscitation via POC thrombelastography. Ann Surg. 251(4): p. 604-614.
Kashuk et al. The emerging role of rapid thromboelastography in trauma care. J Trauma 67, 417-418, (2009).
Kasirer-Friede et al. (2002) Lateral clustering of platelet GP Ib-IX complexes leads to up-regulation of the adhesive function of integrin alpha IIbbeta 3. J Biol Chem 277(14):11949-11956.
Kasirer-Friede et al. (2004) Signaling through GP Ib-IX-V activates alpha IIb beta 3 independently of other receptors. Blood 103(9):3403-3411.
Katori et al. (2005) The effects of platelet count on clot retraction and tissue plasminogen activator-induced fibrinolysis on thrombelastography. Anesth Analg. 100(6): p. 1781-1785.
Kaufmann et al. (1997) Usefulness of thrombelastography in assessment of trauma patient coagulation. J Trauma. 42(4): p. 716-720; discussion 720-722.
Kaunas et al. Cooperative effects of Rho and mechanical stretch on stress fiber organization. Proc Natl Acad Sci U S A 102: 15895-15900, 2005.
Kelly et al. (2008) Injury severity and causes of death from Operation Iraqi Freedom and Operation Enduring Freedom: 2003-2004 versus 2006. J Trauma. 64(2 Suppl): p. S21-S26; discussion S26-7.
Kroll et al. (1991) von Willebrand factor binding to platelet Gplb initiates signals for platelet activation. J Clin Invest 88(5):1568-1573.
Lam et al. (2011) Mechanics and contraction dynamics of single platelets and implications for clot stiffening. Nature materials 10(1):61-66.
Langille BL. Morphologic responses of endothelium to shear stress: reorganization of the adherens junction. Microcirculation 8: 195-206, 2001.
Le Duc et al. Vinculin potentiates E-cadherin mechanosensing and is recruited to actin-anchored sites within adherens junctions in a myosin II-dependent manner. J Cell Biol 189: 1107-1115, 2010.

(56) References Cited

OTHER PUBLICATIONS

Lemmon et al. (2005) Shear force at the cell-matrix interface: enhanced analysis for microfabricated post array detectors. Mech Chem Biosyst. 2(1): p. 1-16.
Leng et al. (1998) RhoA and the function of platelet integrin alphaIIb-beta3. Blood. 91(11): p. 4206-4215.
Leon et al. (2007) Megakaryocyte-restricted MYH9 inactivation dramatically affects hemostasis while preserving platelet aggregation and secretion. Blood. 110(9): p. 3183-3191.
Levrat et al. (2008) Evaluation of rotation thrombelastography for the diagnosis of hyperfibrinolysis in trauma patients. Br J Anaesth. 100(6): p. 792-797.
Li et al. (2003). Detection of single micron-sized magnetic bead and magnetic nanoparticles using spin valve sensors for biological applications. Journal of Applied Physics 93(10): 7557-7559.
Liang et al. Platelet retraction force measurements using flexible post force sensors. Lab Chip 10: 991-998, 2010.
Liu et al. (2010) Mechanical Forces in Endothelial Cells During Firm Adhesion and Early Transmigration of Human Monocytes. Cellular and Molecular Bioengineering. 3(1): p. 50-59.
Liu et al. Mechanical tugging force regulates the size of cell-cell junctions. Proc Natl Acad Sci U S A 107: 9944-9949, 2010.
Maani et al. (2009) Coagulopathy in traumapatients: what are the main influence factors? Current Opinion in Anesthesiology. 22(2): p. 255-260.
Maeda et al. (2005) Increased tyrosine phosphorylation of platelet proteins including pp125(FAK) suggests endogenous activation and aggregation in pulmonary hypertension. Clin Appl Thromb Hemost. 11(4): p. 411-415.
Mailhac et al. (1994) Effect of an eccentric severe stenosis on fibrin(ogen) deposition on severely damaged vessel wall in arterial thrombosis. Relative contribution of fibrin(ogen) and platelets. Circulation 90(2):988-996.
Martini et al. Thrombelastography is better than PT, aPTT, and activated clotting time in detecting clinically relevant clotting abnormalities after hypothermia, hemorrhagic shock and resuscitation in pigs. J Trauma 65, 535-543, (2008).
Martins et al. (2010). Challenges and trends in the development of a magnetoresistive biochip portable platform. Journal of Magnetism and Magnetic Materials 322(9-12): 1655-1663.
Maruthamuthu et al. Cell-ECM traction force modulates endogenous tension at cell-cell contacts. Proc Natl Acad Sci U S A 108: 4708-4713, 2011.
Mazzucato et al. (2002) Sequential cytoplasmic calcium signals in a 2-stage platelet activation process induced by the glycoprotein Ibalpha mechanoreceptor. Blood 100(8):2793-2800.
Mehta et al. Signaling mechanisms regulating endothelial permeability. Physiol Rev 86: 279-367, 2006.
Miao et al. Effects of flow patterns on the localization and expression of VE-cadherin at vascular endothelial cell junctions: in vivo and in vitro investigations. J Vasc Res 42: 77-89, 2005.
Moore et al. (2010) Stretchy proteins on stretchy substrates: the important elements of integrin-mediated rigidity sensing. Dev Cell. 19(2): p. 194-206.
Morii et al. (1992) A rho gene product in human blood platelets. II. Effects of the ADP-ribosylation by botulinum C3 ADP-ribosyltransferase on platelet aggregation. J Biol Chem. 267(29): p. 20921-20926.
Mrksich, M. (2009) Using self-assembled monolayers to model the extracellular matrix. Acta Biomater. 5(3): p. 832-841.
Nance M. (ed), National Trauma Data Bank Annual Report 2011.
Nelson et al. (2003) Degradation of micropatterned surfaces by cell-dependent and -independent processes. Langmuir. 19(5): p. 1493-1499.
Nelson et al. (2005) Emergent patterns of growth controlled by multicellular form and mechanics. Proc Natl Acad Sci U S A. 102(33): p. 11594-11599.
Nesbitt et al. (2009) A shear gradient-dependent platelet aggregation mechanism drives thrombus formation. Nat Med. 15(6): p. 665-673.

Ni et al. (2003) Plasma fibronectin promotes thrombus growth and stability in injured arterioles. Proc Natl Acad Sci U S A. 100(5): p. 2415-2419.
Nieswandt et al. (2003) Platelet-collagen interaction: is GPVI the central receptor? Blood 102(2):449-461.
Niles et al. Increased mortality associated with the early coagulopathy of trauma in combat casualties. J Trauma 64, 1459-1463; discussion 1463-1455, (2008).
Noria et al. Transient and steady-state effects of shear stress on endothelial cell adherens junctions. Circ Res 85: 504-514, 1999.
Okorie et al. (2006) Matrix protein microarrays for spatially and compositionally controlled microspot thrombosis under laminar flow. Biophys J. 91(9): p. 3474-3481.
Ono et al. (2008) Identification of a fibrin-independent platelet contractile mechanism regulating primary hemostasis and thrombus growth. Blood. 112(1): p. 90-99.
Phelps et al. Spatial variations in endothelial barrier function in disturbed flows in vitro. Am J Physiol Heart Circ Physiol 278: H469-476, 2000.
Plotkin et al. (2008) A reduction in clot formation rate and strength assessed by thrombelastography is indicative of transfusion requirements in patients with penetrating injuries. J Trauma. 64(2 Suppl): p. S64-S68.
Pokutta et al. Structure and mechanism of cadherins and catenins in cell-cell contacts. Annu Rev Cell Dev Biol23: 237-261, 2007.
Potard et al. Cytoskeletal mechanics in confluent epithelial cells probed through integrins and E-cadherins. Am J Physiol 272: C1654-1663, 1997.
Reininger AJ, et al. (2006) Mechanism of platelet adhesion to von Willebrand factor and microparticle formation under high shear stress. Blood 107(9):3537-3545.
Reininger, A.J., Function of von Willebrand factor in haemostasis and thrombosis. Haemophilia, 2008. 14 Suppl 5: p. 11-26.
Rossaint et al.(2010) Management of bleeding following major trauma: an updated European guideline. Critical Care. 14(2): p. 1-29.
Rugeri et al. (2007) Diagnosis of early coagulation abnormalities in trauma patients by rotation thrombelastography. J Thromb Haemost. 5(2): p. 289-295.
Ruggeri et al. (2006) Activation-independent platelet adhesion and aggregation under elevated shear stress. Blood. 108(6): p. 1903-1910.
Ruggeri, Z.M. (2009) Platelet adhesion under flow. Microcirculation. 16(1): p. 58-83.
Sanchez-Cortes et al.(2009) The platelet integrin alphaIIbbeta3 binds to the RGD and AGD motifs in fibrinogen. Chem Biol. 16(9): p. 990-1000.
Savage et al. (1996) Initiation of platelet adhesion by arrest onto fibrinogen or translocation on von Willebrand factor. Cell 84(2):289-297.
Savage et al. (1998) Specific synergy of multiple substrate-receptor interactions in platelet thrombus formation under flow. Cell. 94(5): p. 657-666.
Savage et al. (1992) Modulation of platelet function through adhesion receptors. A dual role for glycoprotein IIb-IIIa (integrin alpha IIb beta 3) mediated by fibrinogen and glycoprotein Ib-von Willebrand factor. J Biol Chem. 267(16): p. 11300-11306.
Savage et al. (2002) Functional self-association of von Willebrand factor during platelet adhesion under flow. Proc Natl Acad Sci U S A. 99(1): p. 425-430.
Schmitt et al. Trauma in Washington State, A Chart Report of the First 15 Years 1995-2009. DOH 689-001, Feb. 2011.
Schochl et al. Goal-directed coagulation management of major trauma patients using thromboelastometry (ROTEM)-guided administration of fibrinogen concentrate and prothrombin complex concentrate. Grit Care 14, R55, (2010).
Schoenwaelder et al. (2002) RhoA sustains integrin alpha IIbbeta 3 adhesion contacts under high shear. J Biol Chem. 277(17): p. 14738-14746.
Seattle & King County Division of Emergency Medical Services: 2012 Annual Report.
Shankaran et al. (2003) Aspects of hydrodynamic shear regulating shear-induced platelet activation and self-association of von Willebrand factor in suspension. Blood 101(7):2637-2645.

(56) References Cited

OTHER PUBLICATIONS

Shattil et al. (1998) Integrin signaling: the platelet paradigm. Blood. 91(8): p. 2645-2657.
Shattil et al. (2010) The final steps of integrin activation: the end game. Nat Rev Mol Cell Biol 11(4):288-300.
Shay-Salit et al. VEGF receptor 2 and the adherens junction as a mechanical transducer in vascular endothelial cells. Proc Natl Acad Sci US A 99: 9462-9467, 2002.
Shinjo, T., Nanomagnetism and Spintronics. (2009), Elsevier B.V. Boston.
Shiu et al. Rho mediates the shear-enhancement of endothelial cell migration and traction force generation. Biophys J 86: 2558-2565, 2004.
Siedlecki et al. Shear-dependent changes in the three-dimensional structure of human von Willebrand factor. Blood, 1996. 88(8): p. 2939-2950.
Simmons et al. (1969) Coagulation disorders in combat casualties. I. Acute changes after wounding. II. Effects of massive transfusion. 3. Post-resuscitative changes. Ann Surg. 169(4): p. 455-482.
Sniadecki et al. (2007) Microfabricated silicone elastomeric post arrays for measuring traction forces of adherent cells. Methods Cell Biol. 83: p. 313-328.
Sniadecki et al. (2001) A Silicon Microfluidic Multiplexer Using Field Effect Flow Control. in Micro Total Analysis Systems 2001. Monterey, California: Kluwer, 1 pg.
Sniadecki et al. (2004) Induced pressure pumping in polymer microchannels via field-effect flow control. Anal Chem. 76(7): p. 1942-1947.
Sniadecki et al. (2007) Magnetic microposts as an approach to apply forces to living cells. Proc Natl Acad Sci U S A. 104(37): p. 14553-14558.
Sniadecki et al. (2008) Magnetic microposts for mechanical stimulation of biological cells: fabrication, characterization, and analysis. Review of Scientific Instruments. 79(4): p. 044302.
Solomon et al. Platelet function following trauma. A multiple electrode aggregometry study. Thromb Haemost 106, 322-330, (2011).
Sorensen et al. (2012). Emerging treatment strategies for trauma-induced coagulopathy. Br J Surg 99 Suppl 1: 40-50.
Spalding et al. (2007). Cost reduction of perioperative coagulation management in cardiac surgery: value of "bedside" thrombelastography (ROTEM). Eur J Cardiothorac Surg 31(6): 1052-1057.
Strony et al. (1993) Analysis of shear stress and hemodynamic factors in a model of coronary artery stenosis and thrombosis. Am J Physiol 265(5 Pt 2):H1787-1796.
Szanto et al. (2012) New insights into von Willebrand disease and platelet function. Seminars in thrombosis and hemostasis 38(1):55-63.
Tambe et al. Collective cell guidance by cooperative intercellular forces. Nature Materials 10: 469-475, 2011.
Tan et al. (2003) Cells lying on a bed of microneedles: an approach to isolate mechanical force. Proc Natl Acad Sci U S A. 100(4): p. 1484-1489.
Tan et al. (2004) Simple approach to micropattern cells on common culture substrates by tuning substrate wettability. Tissue Eng. 10(5-6): p. 865-872.
Ting et al. (2012). Flow mechanotransduction regulates traction forces, intercellular forces, and adherens junctions. Am J Physiol Heart Circ Physiol 302(11): H2220-2229.
Tovar-Lopez et al. A microfluidics device to monitor platelet aggregation dynamics in response to strain rate micro-gradients in flowing blood. Lab Chip, 2010. 10(3): p. 291-302.
Trepat et al. Physical forces during collective cell migration. Nat Phys 5: 426-430, 2009.
Turitto et al. (1980) Red blood cells: their dual role in thrombus formation. Science. 207(4430): p. 541-543.
Tzima E. Role of small GTPases in endothelial cytoskeletal dynamics and the shear stress response. Circ Res 98: 176-185, 2006.
Tzima et al. Activation of integrins in endothelial cells by fluid shear stress mediates Rho-dependent cytoskeletal alignment. Embo J 20: 4639-4647, 2001.
Tzima et al. Activation of Rac1 by shear stress in endothelial cells mediates both cytoskeletal reorganization and effects on gene expression. Embo J 21: 6791-6800, 2002.
Tzima et al. Localized cdc42 activation, detected using a novel assay, mediates microtubule organizing center positioning in endothelial cells in response to fluid shear stress. J Biol Chem 278: 31020-31023, 2003.
Ukropec et al. Regulation of VE-cadherin linkage to the cytoskeleton in endothelial cells exposed to fluid shear stress. Exp Cell Res 273: 240-247, 2002.
Vidreicher et al. (2007) Dynamic interaction between Src and C-terminal Src kinase in integrin alphaIIbbeta3-mediated signaling to the cytoskeleton. J Biol Chem. 282(46): p. 33623-33631.
Weisel, J.W. (2007) Structure of fibrin: impact on clot stability. J Thromb Haemost. 5 Suppl 1: p. 116-124.
Weisenberg et al. (2002). Hemocompatibility of materials used in microelectromechanical systems: Platelet adhesion and morphology in vitro. Journal of Biomedical Materials Research 60(2): 283-291.
White et al. Coagulopathy and traumatic shock: characterizing hemostatic function during the critical period prior to fluid resuscitation. Resuscitation 81, 111-116, (2010).
Whitesides et al. Soft lithography in biology and biochemistry. Annu Rev Biomed Eng 3, 335-373, (2001).
Wohlauer et al. (2012). Early platelet dysfunction: an unrecognized role in the acute coagulopathy of trauma. J Am Coll Surg 214(5): 739-746.
Wojciak-Stothard et al. Shear stress-induced endothelial cell polarization is mediated by Rho and Rac but not Cdc42 or PI 3-kinases. J Cell Biol 161: 429-439, 2003.
Xia et al. (1998) Soft lithography. Angewandte Chemie-International Edition. 37(5): p. 551-575.
Yamada et al. Deconstructing the cadherin-catenin-actin complex. Cell 123: 889-901, 2005.
Yang et al. (2007) Geometric considerations of micro- to nanoscale elastomeric post arrays to study cellular traction forces. Advanced Materials. 19(20): p. 3119-3123.
Yonemura et al. alpha-Catenin as a tension transducer that induces adherens junction development. Nat Cell Biol 12: 533-542, 2010.
Yoshigi et al. Quantification of stretch-induced cytoskeletal remodeling in vascular endothelial cells by image processing. Cytometry A 55: 109-118, 2003.
International Search Report and Written Opinion for Application No. PCT/US2014/044448; Applicant: University of Washington Through its Center for Commercialization; Date of Mailing: Oct. 22, 2014 (16 pages).

\* cited by examiner

MICROFLUIDIC DEVICES FOR MEASURING PLATELET COAGULATION AND ASSOCIATED SYSTEMS AND METHODS

CROSS-REFERENCE TO RELATED APPLICATIONS

This present application is a U.S. National Phase application of International Application No. PCT/US2013/031782, filed Mar. 14, 2013, which claims the benefit of the following provisional applications:

(a) U.S. Provisional Patent Application No. 61/645,191, filed May 10, 2012;
(b) U.S. Provisional Patent Application No. 61/709,809, filed Oct. 4, 2012;
(c) U.S. patent application Ser. No. 13/663,339, filed Oct. 29, 2012; and
(d) U.S. Provisional Patent Application No. 61/760,849, filed Feb. 5, 2013.

All of the foregoing applications are incorporated herein by reference in their entireties. Further, components and features of embodiments disclosed in the applications incorporated by reference may be combined with various components and features disclosed and claimed in the present application.

STATEMENT REGARDING FEDERALLY-SPONSORED RESEARCH

This invention was made with government support under N66001-11-1-4129 awarded by SPAWAR—Space and Naval Warfare Systems Center (SSC). The government has certain rights in the invention.

TECHNICAL FIELD

The present technology relates generally to microfluidic devices for measuring platelet coagulation, and associated systems and methods.

BACKGROUND

Platelets are essential for staunching blood loss in order for tissue to heal. At a wound site, platelets undergo a coagulation process of activation, shape change, secretion, and aggregation that ultimately leads to a hemostatic clot containing fibrin strands and platelets. Platelets play a unique biomechanical role in hemostasis: their actin-myosin forces strengthen their integrin adhesions and prevent fibrinolysis by pulling fibrin strands and platelets closer together.

Hemodynamics play an important role in the activity of platelets. High shear rate gradients can occur at locations where blood vessels bend, branch, or narrow, and can arise at a vascular stent or artificial valve. These shear gradients have been observed to cause platelets to adhere to the vessel wall, leading to their activation and aggregation. High shear gradients can cause a self-sustaining process where platelet aggregation increases the local shear gradient, further causing platelets to adhere and aggregate.

The primary method by which the body responds to injury is the formation of clots to stop bleeding. The strength of a clot is largely dependent on the ability of platelet cells trapped within it to contract forcefully, which stiffens the fibrin meshwork surrounding the platelets and secures the clot to the wound to prevent rupture. Proper clot formation is critical in trauma patients, since impaired clot formation is associated with a significant increase in mortality. For example, trauma patients with platelet dysfunction can have greater injury severity and worsening shock. They may require more blood transfusions and have greater mortality rates. Patients with such conditions need to be put on more rapid transport from the scene of injury and can be triaged with "damage control" interventions, such as a hypotensive resuscitation strategy. Upon hospital arrival, these patients can be given earlier and more aggressive treatments, including tailored blood product transfusions, and can be more quickly escalated to immediate surgery.

Traditional diagnostic tests that determine whether platelets are adequately coagulating are technically complex and require a significant amount of blood for testing. Further, such tests can take a significant amount of time for a complete reading. This processing time can cause delay in potential treatment techniques for trauma patients, thereby increasing their chance of a negative outcome.

DETAILED DESCRIPTION

The present technology relates generally to microfluidic devices for measuring platelet coagulation, and associated systems and methods. In some embodiments, a fluidics device includes an array of microstructures including pairs of generally rigid blocks and generally flexible posts. The fluidics device further includes at least one fluid channel configured to accept the array. The fluid channel is configured to induce fluid flow of a biological sample, such as whole blood, through the array. The fluidics device can further include a detection component configured to measure a degree of deflection of one or more of the flexible posts in the array. In some embodiments, the fluidics device comprises a handheld device and usable for point of care testing of platelet forces and coagulation.

Specific details of several embodiments of the technology are described below with reference to FIGS. 1A-6. Other details describing well-known structures and systems often associated with cellular research tools or point-of-care fluidic devices have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1A-6.

Figure 1A:
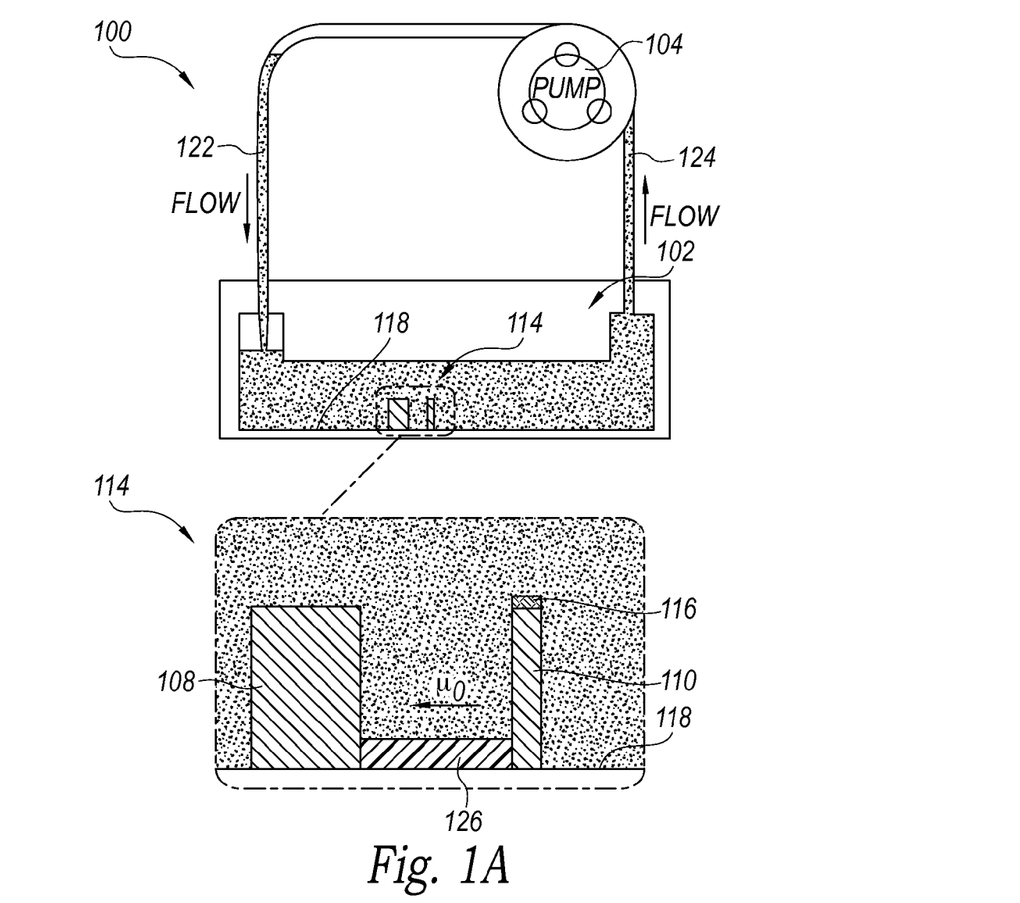
FIG. 1A is a partially schematic illustration of a microfluidic flow chamber configured in accordance with embodiments of the technology.

FIG. 1A is a partially schematic illustration of a fluid flow chamber 100 configured in accordance with embodiments of the technology. The chamber 100 can include a main channel 102 through which fluid flows from an inlet 122 to an outlet 124. In several embodiments, the fluid can comprise whole blood or platelets, or other fragments of whole blood including plasma and plasma proteins. In other embodiments, the fluid can comprise at least one of endothelial cells, circulating tumor cells, cancer cells, fibroblasts, smooth muscle cells, cardiomyocytes, red blood cells, white blood cells, bacteria, megakaryocytes, enzymes, minerals, biominerals, or fragments thereof. While FIG. 1A illustrates a single main channel 102, in further embodiments the chamber 100 can include a plurality of fluid channels. In embodiments with multiple fluid channels, a user can introduce different fluids, biological samples, and/or reagents in the different channels. Or, as will be described in further detail below, the chamber 100 can include multiple fluid channels able to operate in parallel and test different features of a fluid sample. For example, the chamber 100 can test a control sample against a modified sample, or can introduce a sample into multiple fluid channels having different surface chemistries.

The main channel 102 is configured to accept one or more arrays 114 of microstructures, such as microposts. In several embodiments, the array 114 is positioned at or near a base or bottom 118 of the main channel 102 such that fluid can flow substantially over and through the array 114. As will be described in further detail below, in some embodiments, the array 114 comprises one or more pairs of microstructures. In some cases, each pair of microstructures includes a generally rigid block 108 proximate to a generally flexible post 110. As will be discussed in further detail below, in some embodiments the top of the post 110 comprises a magnetic tip 116. The magnetic tip 116 on the top of the post 110 can be made of cobalt, nickel, samarium, or other rare earth metals grown by electrochemical deposition in the pores of a template. In other embodiments, the magnetic tip 116 comprises other materials or is formed or deposited by other methods.

In several formations, the block 108 is upstream of the downstream post 110. In some embodiments, the block 108 and post 110 are spaced apart by 5-15 μm, and in a particular embodiment are spaced apart by 9 μm. In various embodiments, the array 114 can include other combinations of blocks 108 and posts 110. For example, the ratio of blocks 108 to posts 110 may not be 1:1, but instead there can be multiple posts 110 proximate to a single block 108. In further embodiments, this proportion is reversed. In still further embodiments, the post 110 is upstream of the block 108. The post 110 can act as an elastic, cantilever beam which deflects in proportion to the force applied at its upper tip. For example, the deflection can be a continuum from the post 110 base to tip. In several embodiments, the post 110 deflects significantly more than the block 108. In some cases, the deflection of the block 108 is negligible or non-existent.

The array 114 can also include one or more spin valves 126 under or adjacent to one or more posts 110 or blocks 108. For example, there may be a spin valve 126 for each block-and-post pair of microstructures, and the spin valve 126 can be positioned between the block 108 and post 110. As will be described in further detail below, the spin valve 126 can be used to measure changes in the magnetic field caused by the magnetic tip 116 of the post 110 deflecting toward the block 108. The spin valve 126 can use the giant magnetorestrictive (GMR) effect in thin films. The spin valve 126 can include a strip of thin film metals sputtered in alternating stacks of magnetic and non-magnetic layers. Due to the interactions of the spins of the electrons in the different layers, the resistance of the strip is sensitive to changes in the in-plane magnetic field. The spin valve 126 may have magnetic sensitivity on the order of 1 nT, which can achieve a 20:1 signal-to-noise ratio. In some embodiments, the change in resistance of the spin valve 126 can be measured by setting up a Wheatstone bridge configuration.

In several embodiments, the flow chamber 100 is sized for point-of-care use. For example, the flow chamber 100 may be sized to receive a relatively small sample (e.g., less than 3 μl) of fluid such as blood. In some embodiments, a drop of blood is sufficient to operate the device. In one embodiment, the main channel 102 has a length of 2 cm, a width of 4 mm, and a depth of 0.5 mm. The main channel 102 can have other dimensions in other embodiments. In several embodiments, the flow chamber 100 is hermetically sealed. As will be described below with reference to FIG. 3, in some embodiments, all or a portion of the chamber 100 or the array 114 comprises a card configured to be placed within a handheld device that activates a fluidic test or reads the test results (e.g., the magnitude of platelet forces).

Figure 1B:
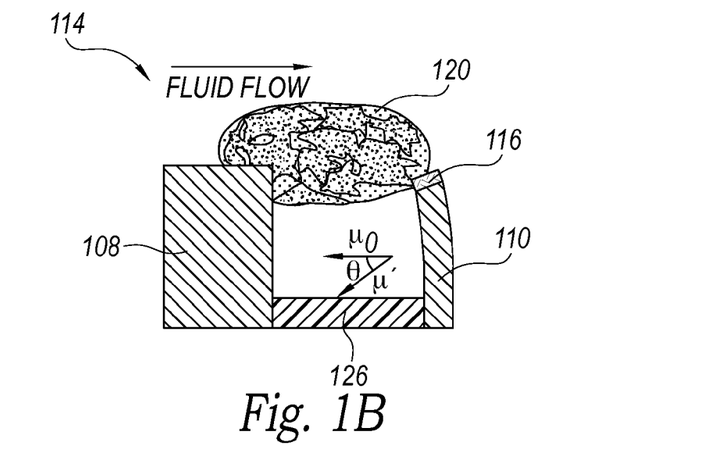
FIG. 1B is a partially schematic illustration of an array of microposts undergoing fluid flow in the chamber of FIG. 1A in accordance with embodiments of the technology.

FIG. 1B is a partially schematic view of the microstructure array 114 of FIG. 1A undergoing fluid flow and configured in accordance with embodiments of the technology. Referring to FIGS. 1A and 1B together, in operation, the array 114 is placed in the main channel 102 and exposed to fluid flow conditions (e.g., laminar flow conditions to create shear gradient in the array 114) for a selected time period. For example, in some embodiments, the array 114 can be placed inside the channel 102 and whole blood fluid flow can be applied continuously for less than a minute. In other embodiments, the flow can be applied intermittently or for more or less than a minute. For example, the flow may be provided for one minute or less, five minutes or less, or fifteen minutes or less. In several embodiments, the flow can be provided without user mixing or other intervention required.

In various embodiments, the term "fluid flow" can refer to pumped or otherwise mechanically moved fluid, pressurized fluid (e.g., introduced via a syringe), or can refer to immersion (without pumping). While a flow unit (e.g., a pump) 104 is shown as connected to the flow chamber 100 and configured to recirculate the media through the chamber 100 and provide static, laminar, and/or disturbed flow in the direction of the flow arrows, in other embodiments the flow unit 104 is absent and the fluid sample is introduced to the main channel 102 via the inlet 122. For example, the fluid sample can be collected (e.g., in heparin or other anticoagulant tubes) and loaded into a syringe and pumped through the main channel 102 at wall shear rates between physiologically normal (2000 s−1) and pathologically high (12000 s−1). In some embodiments, the fluid sample can be withdrawn from the main channel 102 via the outlet 124, while in other embodiments the fluid sample remains in the main channel 102 after testing for ease of disposal. In embodiments having a flow unit 104, the flow unit 104 can comprise a positive displacement pump, a piezoelectric pump, a partial vacuum, a diaphragm pump, a peristaltic pump, a hydrostatic pump, or another device.

As the fluid sample (e.g., whole blood) is introduced into the main channel 102, flowing platelets quickly adhere to the microstructures (e.g., above and between the block 108 and post 110) to form a microscale clot 120. More specifically, platelets aggregate at the clot 120, which forms a mechanical bridge between the block 108 and post 110 structures in the array 114. The platelets contract under the shear forces, causing the post 110 to bend toward the block 108 as an elastic, cantilever beam which deflects in proportion to the force applied at its tip. The degree of post 110 deflection can be used to quantify how much force the platelets in the blood are producing, which can accordingly identify any coagulation deficiencies. In several embodiments, the block 108 and post 110 are spaced close enough together to discourage red blood cells and white blood cells from residing in the clot space between the block 108 and post 110.

To measure the deflection of a post 110, the difference between the position of its tip and base can be analyzed from phase contrast fluorescent microscopy images taken at the top and bottom of the array 114. The magnitude and direction of each traction force (F) can be computed from the deflection ($\delta$) through the relationship:

$$F = \frac{3\pi E D^4}{64 L^3} \delta$$

The length L and diameter D of the microstructures in the array can be measured using a scanning electron microscope. In some embodiments, the diameter of the post 110 is 2.2 μm and the length is 7 μm. Young's modulus of the post material (e.g., polydimethylsiloxane (PDMS), E=2.5 MPa) can be determined by tensile testing.

The magnetic tip 116 on the post 110 can be used to measure platelet forces with a magnetic detection component. For example, the magnetic tip 116 can have a dipole moment $\mu_0$ oriented parallel to the spin valve 126. In the case of a nickel magnetic tip 116, the initial dipole moment will be 4.8 pAm². Assuming the magnetic tip 116 is approximately 60 μm from the sensor, its dipole moment will produce an in-plane magnetic field of $\mu_0$=4.4 μT. This measurement will be the baseline reading for an unbent post 110.

When platelet forces bend the post 110 toward the block 108, the magnetic tip 116 rotates by angle θ. Due to reorientation of the magnetic tip's 116 dipole moment μ', there is a decrease in the in-plane magnetic field measured at the spin valve 126. In a particular embodiment, a 40 nN force is produced by the clot 120. So, based upon a 221 nN/μm spring constant for a post 110 made of SU-8, there will be an approximately 0.3° rotation at the magnetic tip 116 of the post 110. This rotation will cause the magnetic tip's 116 dipole moment if to change its orientation by 0.3° as well, which will cause a drop of $\mu_0 - \mu' = 20$ nT in the in-plane magnetic field measured by the spin valve 126. While a drop of 20 nT may be too small for most low-cost commercial magnetometers (e.g., a Hall effect sensor or fluxgate magnetometer), the spin valve 126 can be sensitive enough to detect such a change in the magnetic field. As will be discussed below with reference to FIG. 2, the array 114 can also include contact pads that allow for connection between the spin valve 126 and electronic equipment for detecting platelet forces.

In other embodiments, other magnetic components, such as magnetic nanowires, can be embedded in or placed within or along other sections of the post 110. For example, in some embodiments, a nanowire is embedded in approximately at least the top ⅔ of the post 110 and is used for magnetic detection. Post deflection using nanowires can be detected using a magnetometer, e.g. spin valve or GMR sensor placed adjacent to (e.g., underneath) the magnetized array 114. In still further embodiments, magnets are omitted from the post 110 and measurements of platelet forces on posts 110 can be conducted using optical microscopy and image processing. Certain optical detection components to detect forces on posts 110 can include a phase contrast microscope, a fluorescence microscope, a confocal microscope, or a photodiode. Other optical detection components can be used in further embodiments.

The arrays 114 discussed above can be manufactured using various templating or molding techniques. For example, in some embodiments, the array 114 may be created by casting a film of PDMS or similar material with a 0.25 mm thickness on a No. 2 glass coverslip. In other embodiments, other materials and/or thicknesses of materials can be used. In some embodiments, the individual microstructures comprise silicon, polymers, metal, or ceramics. In a particular embodiment, individual posts 110 are made using SU-8 photoresist, having a spring constant of about 221 nN/μm. In some embodiments, the microstructures or other portion of the chamber 100 can be substantially coated in a non-fouling coating.

The array 114 of microstructures can be micromolded into desired shapes, arrangements, or patterns. For example, in some embodiments, individual blocks 108 are generally rectangular shaped, with sharp corners configured to generate high shear forces. In other embodiments, the blocks 108 have other shapes such as wedges, triangles, columns, spheres, stars, etc. In a particular embodiment, the block 108 has a height of approximately 10-60 μm, a width of 10-30 μm, and a depth of 5-20 μm. In some embodiments, individual posts 110 are shaped generally as columns, but can have other shapes in further embodiments. In a particular embodiment, the posts 110 have a height of approximately 10-60 μm, and have a diameter of approximately 2-6 μm. In some embodiments, the magnetic tip 116 comprises a layer of nickel about 1 μm thick and about 3 μm in diameter. In further embodiments, the posts 110 can have other dimensions.

It may be desirable to treat or coat the microstructures or other portion of the device 100 with a surface chemistry or binding agent. For example, in some embodiments, a binding element (e.g., fibronectin) can be absorbed onto the surface of a PDMS stamp. The stamps can have no pattern ('flat stamp') or an array of positive relief patterns in the shape of a grid of squares ("square stamps"). Once the binding element is adsorbed, the stamp can be placed into conformal contact with the substrate in order to transfer fibronectin onto the regions of contact. Afterwards, each substrate can be treated with 0.2% Pluronic F127 or other suitable material to ensure that cells adhere to regions where the fibronectin was printed and prevent protein adsorption and block platelet adhesion on the main channel 102. This can help separate the platelets from the other constituents of the blood for testing. In some embodiments, the walls of the main channel 102 are coated with a fluorescent dye and then type I collagen and von Willebrand Factor.

In some embodiments, the individual microstructures (or tips of the microstructures) are substantially coated with at least one surface chemistry or binding element, such as proteins, glycans, polyglycans, glycoproteins, collagen, vitronectin, laminin, monoclonal antibodies, polyclonal antibodies, plasmin, agonists (e.g., thrombin or calcium), matrix proteins (e.g., fibrinogen, fibronectin, von Willebrand Factor), enzymes, minerals, biominerals, inhibitors of actin-myosin activity (e.g., Y-27632, ML-7, or blebbistatin), and/or fragments thereof. In some embodiments, the microstructures are coated with extracellular matrix proteins that enable platelets to attach to them like they would to an injured vessel wall. In some embodiments, microstructures in each microchannel can be stamped with von Willebrand Factor at concentrations in the range of 10-50 μg/ml.

As discussed above, in some embodiments the device 100 includes multiple channels, capable of operating in parallel to test different characteristics of the sample. For example, in some embodiments, the device 100 can include multiple channels, each having a different microstructure surface chemistry. In a particular embodiment, a first microchannel is run as a control channel, a second channel includes a microstructure surface chemistry that encourages clotting, and a third channel includes a microstructure surface chemistry that inhibits platelet coagulation. Multiple channels can be combined to conduct simultaneous testing of a range of clot formation components.

Figure 2:
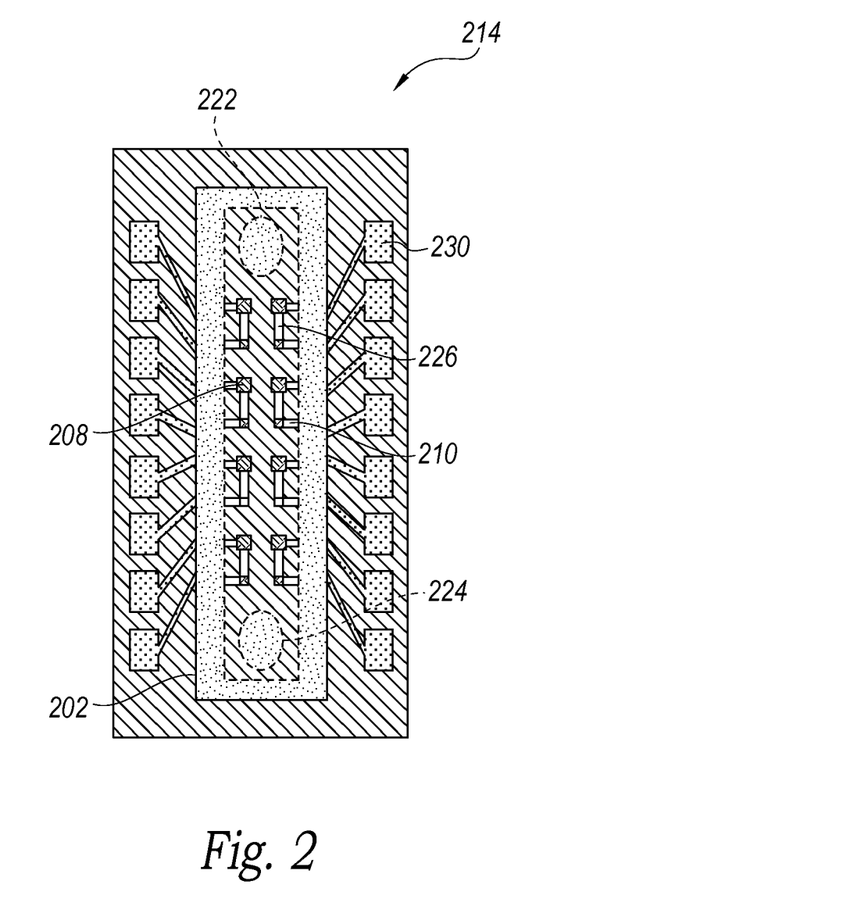
FIG. 2 is a top view of an array of microposts configured in accordance with embodiments of the technology.

FIG. 2 is a top view of an array 214 of microstructures for use in the fluid flow chamber 100 of FIG. 1. The array 214 is received in a microchannel 202 that includes a fluid inlet 222 and fluid outlet 224. The array 214 includes a pattern of pairs of blocks 208 and corresponding downstream posts 210. While the illustrated embodiment includes a grid of pairs of microstructures in rows and columns, in further embodiments the pairs can be placed in different arrangements or there can be more or fewer rows and columns. For example, in some embodiments, there may be 100 each of blocks 208 and posts 210. Further, the blocks 208 and posts 210 need not come in pairs, but instead there may be multiple posts 210 per block 208 (e.g., the posts 210 can encircle the block 208) or there can be multiple blocks 208 per post 210.

A plurality of spin valves 226 are positioned in the array 214, each spin valve 226 between a block 208 and a post 210. One or more contact pads 230 for connecting the spin valves 226 to electronic equipment are located along the edge of the array 214. Data acquisition equipment and signal processing equipment can be used to determine the deflection of the posts 210 in the manner described above. A change in voltage across the spin valves 226 indicates how much force the platelets in a blood sample are producing. If the platelets in a sample are injured, there is a lower change in the voltage measured.

Figure 3:
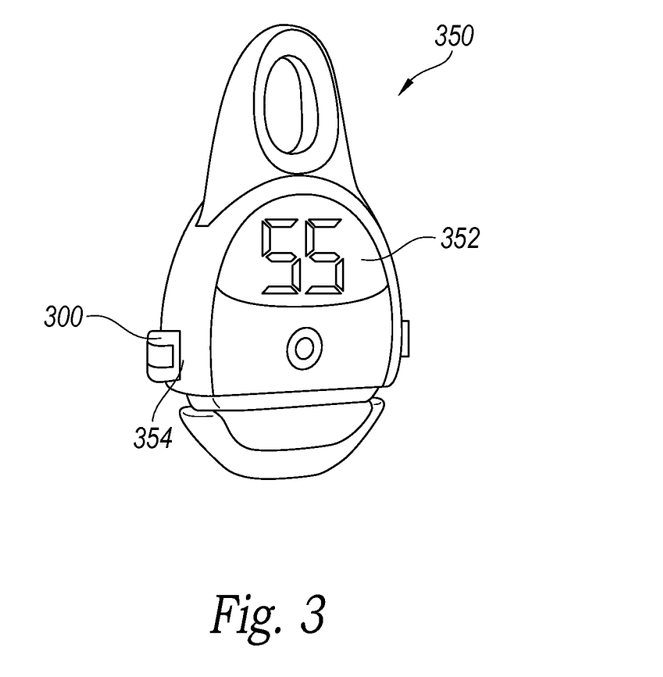
FIG. 3 is a side isometric view of a platelet testing device for measuring platelet forces and configured in accordance with embodiments of the technology.

FIG. 3 is a side isometric view of a platelet testing device 350 for measuring platelet forces and configured in accordance with embodiments of the technology. In some embodiments, the device 350 can comprise an easily portable, handheld size (e.g., having dimensions less than or equal to 10 cm×8 cm×5 cm), point of care testing system. The device 350 can include a receiving portion 354 capable of receiving a sample card 300. The sample card 300 can comprise a flow chamber or array such as the flow chamber 100 or array 114 discussed above with reference to FIG. 1, or portions thereof. In various embodiments, the card 300 can include one fluid channel or multiple channels having different testing conditions (e.g., different microstructure surface chemistries) that are able to operate in parallel. In further embodiments, different cards 300 can be used for different testing conditions. In some embodiments, the device 350 can be reusable, with new fluid samples placed in new or sterilized cards 300. In further embodiments, the testing device 350 is disposable and designed for one-time use.

The testing device 350 can include various electronic components, such as data acquisition equipment and/or signal processing equipment that can couple to the contact pads 230 described above with reference to FIG. 2. Such electronic components can receive and/or process the microstructure deflection data. In some embodiments, the deflection data is processed within the device 350 and an output value of platelet function is generated. Such output data can be relayed to a user via a display 352 on the device 350 or a remote display.

Figure 4:
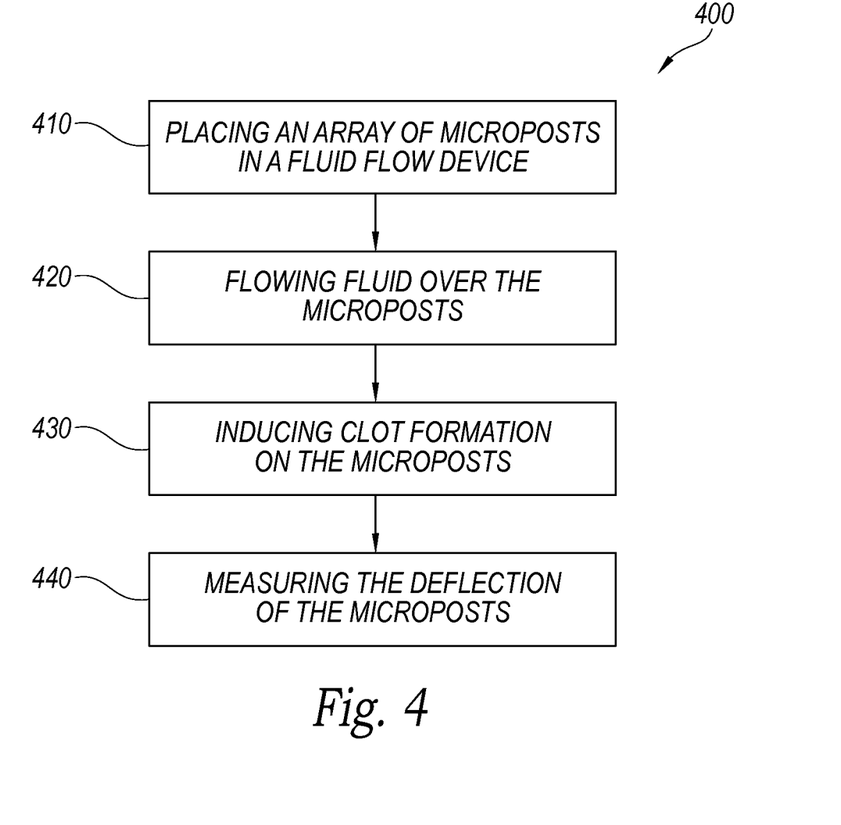
FIG. 4 is a block diagram illustrating a method of measuring platelet coagulation in a biological sample in accordance with embodiments of the technology.

FIG. 4 is a block diagram illustrating a method 400 of measuring platelet coagulation in a biological sample in accordance with embodiments of the technology. At block 410, the method 400 includes placing a block-and-post array of microstructures in a fluid flow device. As discussed above, in several embodiments the block comprises a generally rigid structure that is proximate to a generally flexible post. In some embodiments, the post can include a magnetic tip.

At block 420, the method 400 further includes flowing fluid over the microstructures. In several embodiments, the fluid comprises a blood sample, and in some embodiments is an approximately 3 μl sample of whole blood. The method of flowing fluid can be accomplished in a fluid flow chamber such as the chamber described above with reference to FIG. 1A. In several embodiments, the fluid can be introduced without any flushing or washing steps. At block 430, the method 400 includes inducing a clot formation on the microstructures, such as in a space above and between the block and post. This step can include causing deflection of at least one of the microstructures, such as the post deflecting toward the block. The method 400 can further include measuring the deflection of the microstructures, 440. In several embodiments, the deflection is measured via a magnetic detection assembly, such as through the use of spin valves to measure changes in the magnetic field.

Figure 5A:
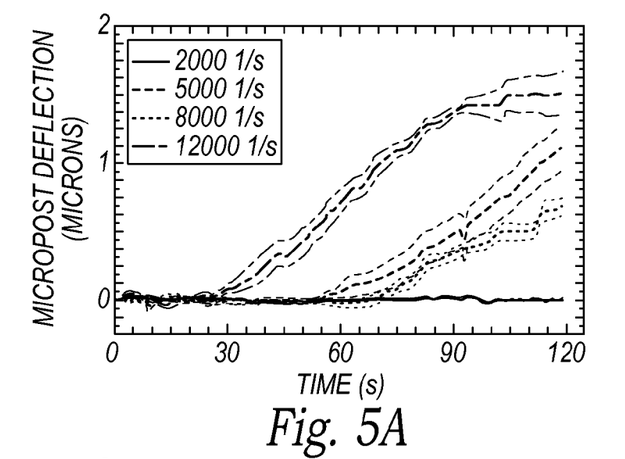
FIGS. 5A-5C are graphs illustrating shear activation required to initiate micropost deflection in three representative patients in accordance with embodiments of the technology.
Figure 5B:
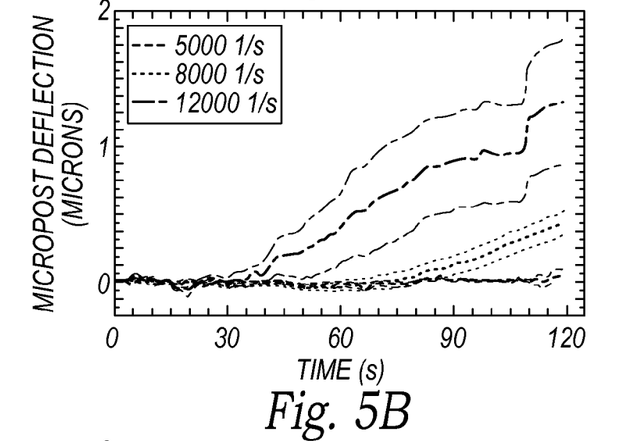
Figure 5C:
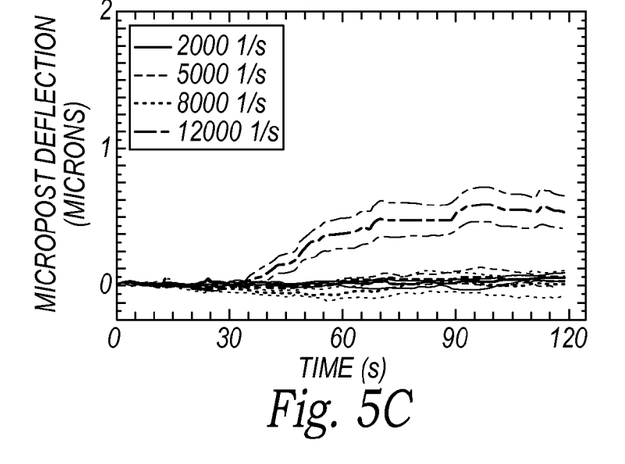

FIGS. 5A-5C are graphs illustrating the shear activation required to initiate micropost deflection in three representative patients (platelet donors) and in accordance with embodiments of the technology. The threshold level of shear activation can be determined by observing the shear gradient needed to cause a micropost deflection in a micropost array in a fluid flow chamber, such as the fluid flow chamber described above with reference to FIG. 1A. As shown, patients have variable levels of shear activation necessary for platelet contraction and corresponding clot formation. Some patients had low shear thresholds for activation, while others had higher shear thresholds. For example, the platelets from the patient of FIG. 5A are inactive at 2,000 l/s, but start generating force at 5000 l/s. In FIG. 5B, the patient's platelets required 8,000 l/s to activate while the patient's platelets in FIG. 5C required 12,000 l/s to activate. This may mean that some of the population is more prone to shear-activation in-vivo. As will be discussed below with reference to FIG. 6, this characteristic can be considered when tailoring therapy or treatment. This could be informative to physicians regarding a patient's platelet activity for antiplatelet treatment or in cases such as post-surgery recovery.

Figure 6:
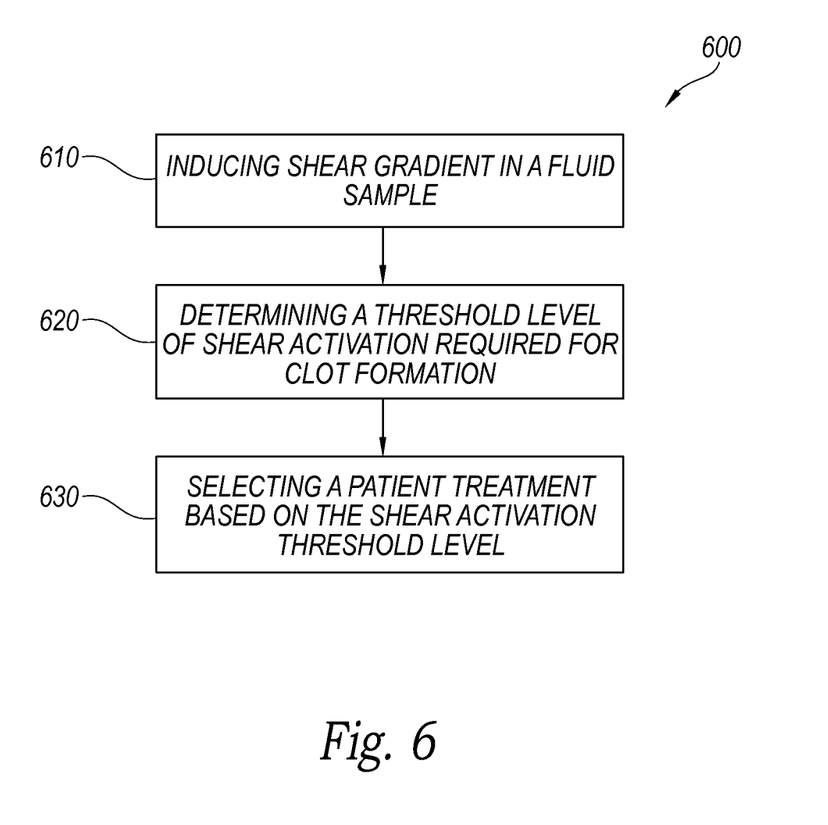
FIG. 6 is a block diagram illustrating a method of selecting a patient treatment in response to the patient's shear activation threshold in accordance with embodiments of the technology.

FIG. 6 is a block diagram illustrating a method 600 of selecting a patient treatment in response to the patient's shear activation threshold in accordance with embodiments of the technology. At block 610, the method includes inducing shear gradient in a fluid sample, such as a sample of blood. The shear gradient can be induced in a fluid flow chamber such as the chamber described above with reference to FIG. 1A. At block 620, the method 600 further includes determining a threshold level of shear activation required for clot formation. The threshold level can be determined by observing the shear gradient needed to cause a micropost deflection in a micropost array in the fluid flow chamber. At block 630, the method 600 includes selecting a treatment for the patient based on the shear activation threshold level. For example, a patient with a low shear threshold that has received an arterial stent may need to have more frequent checks for reocclusion as their platelets may easily bind. In a converse example, a person with a higher shear threshold may not need a high dose of anticoagulant drugs because of an innate resistance to shear activation. The method 600 can thus provide tailored treatment for the particular patient's condition.

EXAMPLES

The following Examples are illustrative of several embodiments of the present technology.

1. A fluidics device, comprising:
an array of microstructures including generally rigid blocks and generally flexible structures;
at least one fluid channel sized to accept the array, wherein the fluid channel is configured to induce fluid flow of a biological sample through the array; and
means for detecting a degree of deflection of one or more of the flexible structures in the array.

2. The device of example 1 wherein the array comprises pairs of the generally rigid blocks and the generally flexible structures.

3. The device of example 1 wherein the microstructures are made from at least one of silicon, polymers, metal, or ceramics.

4. The device of example 1 wherein the means for detecting comprises at least one of an optical detection component or a magnetic detection component.

5. The device of example 4 wherein the magnetic detection component is one of a spin valve, Hall probe, or fluxgate magnetometer.

6. The device of example 4 wherein individual generally flexible structures include a magnetic material.

7. The device of example 6 wherein the magnetic detection component comprises spin valves positioned between individual blocks and generally flexible structures and configured to detect changes in a magnetic field in the array caused by deflection of the generally flexible structures including the magnetic material.

8. The device of example 4 wherein the optical detection component is one of a phase contrast microscope, a fluorescence microscope, a confocal microscope, or a photodiode.

9. The device of example 1 wherein the biological sample comprises at least one of whole blood, plasma, plasma proteins, proteins found in blood or other biological fluids, platelets, endothelial cells, circulating tumor cells, cancer cells, fibroblasts, smooth muscle cells, cardiomyocytes, red blood cells, white blood cells, bacteria, megakaryocytes, or fragments thereof.

10. The device of example 1 wherein at least some of the microstructures are at least partially coated with at least one binding element selected from a group consisting of proteins, enzymes, bioactive minerals, glycans, polyglycans, glycoproteins, collagen, von Willebrand factor, vitronectin, laminin, monoclonal antibodies, polyclonal antibodies, plasmin, agonists, matrix proteins, inhibitors of actin-myosin activity, and fragments thereof.

11. The device of example 1 wherein the fluidics device comprises a handheld-size device.

12. The device of example 1, further comprising a display configured to display a characteristic of the biological sample based on the degree of deflection of the one or more generally flexible structures.

13. An analytic method, comprising:
placing a pair of microstructures in a fluid flow chamber, the pair including a generally rigid block proximate to a generally flexible structure;
flowing fluid over the microstructures; and
measuring a deflection of the generally flexible structure.

14. The method of example 13 wherein placing the pair of microstructures in the fluid flow chamber comprises placing a microstructure at least partially coated in at least one of enzymes, minerals, von Willebrand Factor, a protein, glycan, polyglycan, glycoprotein, collagen, vitronectin, laminin, monoclonal antibody, polyclonal antibody, plasmin, agonist, matrix protein, an inhibitor of actin-myosin activity, or fragments thereof.

15. The method of example 13 wherein flowing fluid over the microstructures comprises flowing a biological fluid over the microstructures.

16. The method of example 15 flowing the biological fluid over the microstructures comprises flowing a biological fluid containing at least one of plasma proteins, minerals, von Willebrand Factor, a protein, glycan, polyglycan, glycoprotein, collagen, vitronectin, laminin, monoclonal antibody, polyclonal antibody, plasmin, agonist, matrix protein, an inhibitor of actin-myosin activity, or fragments thereof.

17. The method of example 13 wherein measuring the deflection of the generally flexible structure comprises using an optical detection component to measure the deflection of the generally flexible structure.

18. The method of example 13 wherein measuring the deflection of the generally flexible structure comprises using a magnetic detection component to measure the deflection of the generally flexible structure.

19. The method of example 18 wherein using the magnetic detection component comprises using one or more of a spin valve, Hall probe, or fluxgate magnetometer to measure a change in a magnetic field caused by the deflection of the generally flexible structure.

20. The method of example 13 wherein placing the pair of microstructures in the fluid flow chamber comprises placing the generally rigid block in a position upstream relative to the generally flexible structure.

21. The method of example 13, further comprising inducing clot formation.

22. A method of selecting a patient treatment, comprising:
inducing shear gradient in a biological fluid sample flowing through a fluid chamber, the fluid chamber including a plurality of microstructures;
determining a threshold level of shear activation required for clot formation of the biological sample on at least one microstructure; and
selecting a treatment for the patient based on the shear activation threshold level.

23. The method of example 22 wherein inducing shear gradient in the biological fluid sample comprises inducing shear gradient in a biological fluid sample containing inhibitors, antagonists, or agonists of the biological fluid sample.

24. The method of example 22 wherein selecting a treatment for the patient comprises selecting a dose of coagulant-inducing or anticoagulant drug based on the shear activation threshold level.

25. The method of example 22 wherein inducing shear gradient in the biological fluid sample comprises inducing shear gradient in a sample of whole blood, plasma, plasma proteins, platelets, endothelial cells, circulating tumor cells, cancer cells, fibroblasts, smooth muscle cells, cardiomyocytes, red blood cells, white blood cells, bacteria, megakaryocytes, or fragments thereof.

26. The method of example 22 wherein inducing shear gradient in the biological fluid sample flowing through the fluid chamber comprises inducing shear gradient in a fluid sample flowing through a fluid chamber having an array of microstructures including generally rigid blocks proximate to generally flexible structures.

27. The method of example 22 wherein determining the threshold level of shear activation comprises measuring a deflection of the microstructures.

The technology disclosed herein offers several advantages over existing systems. For example, the devices disclosed herein can quickly and accurately detect platelet function in emergency point of care settings. The devices can be portable, battery operated, and require little to no warm-up time. A sample need only be a few microliters and can be tested in less than five minutes. Further, the device can be relatively simple, with no moving parts that could mechanically malfunction and no vibration or centrifuge required. Further, such a simple device can be manufactured relatively inexpensively.

From the foregoing it will be appreciated that, although specific embodiments of the technology have been described herein for purposes of illustration, various modifications may be made without deviating from the spirit and scope of the technology. Further, certain aspects of the new technology described in the context of particular embodiments may be combined or eliminated in other embodiments. Moreover, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A fluidics device, comprising:
an array of microstructures including generally rigid blocks and generally flexible structures;
at least one fluid channel sized to accept the array, wherein the fluid channel is configured to induce fluid flow of a biological sample over and through the array; and
a detection component configured to detect a degree of deflection of one or more of the flexible structures in the array,
wherein the generally rigid blocks and the generally flexible structures are positioned within the fluid channel, and wherein the generally rigid blocks are spaced apart from the generally flexible structures along the fluid channel.

2. The device of claim 1 wherein the array comprises pairs of the generally rigid blocks and the generally flexible structures.

3. The device of claim 1 wherein the microstructures are made from at least one of silicon, polymers, metal, or ceramics.

4. The device of claim 1 wherein the detection component comprises a magnetic detection component.

5. The device of claim 4 wherein the magnetic detection component comprises a spin valve, Hall probe, or fluxgate magnetometer.

6. The device of claim 4 wherein at least one of the generally flexible structures includes a magnetic material.

7. The device of claim 4 wherein:
one or more of the generally flexile structures includes a magnetic material; and
the magnetic detection component comprises spin valves, wherein at least one of the spin valves is positioned between at least one of the generally rigid blocks and at least one of the generally flexible structures, and further wherein the magnetic detection components is configured to detect changes in a magnetic field in the array caused by deflection of the one or more generally flexible structures including the magnetic material.

8. The device of claim 1 wherein the detection component comprises an optical detection component, and wherein the optical detection component is a phase contrast microscope, a fluorescence microscope, a confocal microscope, or a photodiode.

9. The device of claim 1 wherein at least some of the microstructures are at least partially coated with at least one binding element selected from a group consisting of proteins, enzymes, bioactive minerals, glycans, polyglycans, glycoproteins, collagen, von Willebrand factor, vitronectin, laminin, monoclonal antibodies, polyclonal antibodies, plasmin, agonists, matrix proteins, inhibitors of actin-myosin activity, and fragments thereof.

10. The device of claim 1 wherein the fluidics device comprises a handheld-size device.

11. The device of claim 1, further comprising a display configured to display a characteristic of the biological sample based on the degree of deflection of the one or more generally flexible structures.

12. A fluidics device, comprising:
an array of microstructures including generally rigid blocks and generally flexible structures;
at least one fluid channel sized to accept the array, wherein the fluid channel is configured to induce fluid flow of a biological sample over and through the array; and
a detection component configured to detect a degree of deflection of one or more of the flexible structures in the array,
wherein the generally rigid blocks and the generally flexible structures are positioned within the fluid channel, and wherein the generally rigid blocks are positioned along the fluid channel upstream of the generally flexible structures.

13. The device of claim 12 wherein the array comprises pairs of the generally rigid blocks and the generally flexible structures.

14. The device of claim 12 wherein the microstructures are made from at least one of silicon, polymers, metal, or ceramics.

15. The device of claim 12 wherein the detection component comprises a magnetic detection component, and wherein the magnetic detection component comprises a spin valve, Hall probe, or fluxgate magnetometer.

16. The device of claim 12 wherein at least one of the generally flexible structures include a magnetic material.

17. The device of claim 12 wherein the magnetic detection component comprises spin valves, and wherein at least one of the spin valves is positioned between at least one of the generally rigid blocks and at least one of the generally flexible structures, and further wherein the magnetic detection component is configured to detect changes in a magnetic field in the array caused by deflection of the generally flexible structures including the magnetic material.

18. The device of claim 12 wherein the detection component comprises an optical detection component, and wherein the optical detection component is one of a phase contrast microscope, a fluorescence microscope, a confocal microscope, or a photodiode.

19. The device of claim 12 wherein at least some of the microstructures are at least partially coated with at least one binding element selected from a group consisting of proteins, enzymes, bioactive minerals, glycans, polyglycans, glycoproteins, collagen, von Willebrand factor, vitronectin, laminin, monoclonal antibodies, polyclonal antibodies, plasmin, agonists, matrix proteins, inhibitors of actin-myosin activity, and fragments thereof.

20. The device of claim 12 wherein the fluidics device comprises a handheld-size device.

21. The device of claim 12, further comprising a display configured to display a characteristic of the biological sample based on the degree of deflection of the one or more generally flexible structures.

* * * * *